(12) United States Patent
Pilgaonkar et al.

(10) Patent No.: US 9,198,862 B2
(45) Date of Patent: Dec. 1, 2015

(54) DISPERSIBLE TABLET COMPOSITION

(75) Inventors: Pratibha Sudhir Pilgaonkar, Mumbai (IN); Maharukh Tehmasp Rustomjee, Mumbai (IN); Anilkumar Surendrakumar Gandhi, Mumbai (IN); Pradnya Bagde, Mumbai (IN); Varsha Barve, Mumbai (IN)

(73) Assignee: Rubicon Research Private Limited, Mumbai (IN)

( * ) Notice: Subject to any disclaimer, the term of this patent is extended or adjusted under 35 U.S.C. 154(b) by 548 days.

(21) Appl. No.: 11/996,266

(22) PCT Filed: Jul. 24, 2006

(86) PCT No.: PCT/IN2006/000291
§ 371 (c)(1),
(2), (4) Date: Mar. 20, 2008

(87) PCT Pub. No.: WO2007/052289
PCT Pub. Date: May 10, 2007

(65) Prior Publication Data
US 2008/0312168 A1  Dec. 18, 2008

(30) Foreign Application Priority Data

Jul. 22, 2005 (IN) .......................... 879/MUM/2005

(51) Int. Cl.
| | | |
|---|---|---|
| A61K 31/70 | (2006.01) | |
| A61K 9/16 | (2006.01) | |
| A61K 9/20 | (2006.01) | |
| A61K 31/55 | (2006.01) | |

(52) U.S. Cl.
CPC ............. *A61K 9/1635* (2013.01); *A61K 9/1652* (2013.01); *A61K 9/2031* (2013.01); *A61K 9/2054* (2013.01); *A61K 9/2077* (2013.01); *A61K 31/55* (2013.01)

(58) Field of Classification Search
CPC . A61K 9/1635; A61K 9/1652; A61K 9/2031; A61K 9/2054; A61K 9/2077; A61K 31/55
USPC .................................................. 424/464, 465
See application file for complete search history.

(56) References Cited

U.S. PATENT DOCUMENTS

| | | | | |
|---|---|---|---|---|
| 4,886,669 | A | * | 12/1989 | Ventouras ...................... 424/469 |
| 5,256,699 | A | | 10/1993 | Murphy et al. |
| 5,262,417 | A | * | 11/1993 | Gammill et al. ......... 514/253.08 |
| 5,629,016 | A | | 5/1997 | Fielden et al. |
| 5,660,860 | A | | 8/1997 | Fielden et al. |
| 5,698,221 | A | | 12/1997 | Patel et al. |
| 5,698,226 | A | | 12/1997 | Fielden |
| 6,605,301 | B2 | * | 8/2003 | Zakarian et al. ............... 424/464 |
| 7,297,683 | B2 | * | 11/2007 | Glover et al. .................... 514/43 |
| 2002/0022056 | A1 | | 2/2002 | Schlutermann |
| 2002/0061333 | A1 | | 5/2002 | Zakarian et al. |
| 2004/0043996 | A1 | | 3/2004 | Nadkarni |
| 2004/0208936 | A1 | * | 10/2004 | Chorin et al. .................. 424/490 |
| 2006/0111343 | A1 | | 5/2006 | Krishnan et al. |
| 2006/0141037 | A1 | | 6/2006 | Mehta et al. |

FOREIGN PATENT DOCUMENTS

| | | |
|---|---|---|
| CA | 2277722 | 7/1992 |
| EP | 0181650 | 5/1986 |
| EP | 0273005 | 6/1988 |
| EP | 0685231 | 12/1995 |
| EP | 1 086 689 | 3/2001 |
| GB | 2278057 | 11/1994 |
| WO | 9961026 | 12/1999 |
| WO | WO 01/45671 A2 | 6/2001 |
| WO | 02094774 | 11/2002 |
| WO | 03104192 | 12/2003 |
| WO | 2004026314 | 4/2004 |
| WO | 2004064810 | 8/2004 |
| WO | 2004103340 | 12/2004 |
| WO | 2005051350 | 6/2005 |
| WO | WO 2005/115347 A1 | 12/2005 |
| WO | 2006046105 | 5/2006 |

OTHER PUBLICATIONS

Schiermeier et al, "Fast dispersible ibuprofen tablets", European Journal of Pharmaceutical Sciences, vol. 15 (2002), pp. 295-305.*

* cited by examiner

*Primary Examiner* — Elli Peselev
(74) *Attorney, Agent, or Firm* — Nigamnarayan Archarya; Rubicon Research Private Limited

(57) ABSTRACT

Disclosed herein is a dispersible tablet composition including a pharmacologically active ingredient and at least one excipient that reduces the sedimentation rate of the active ingredient and a process for preparing the same.

8 Claims, 1 Drawing Sheet

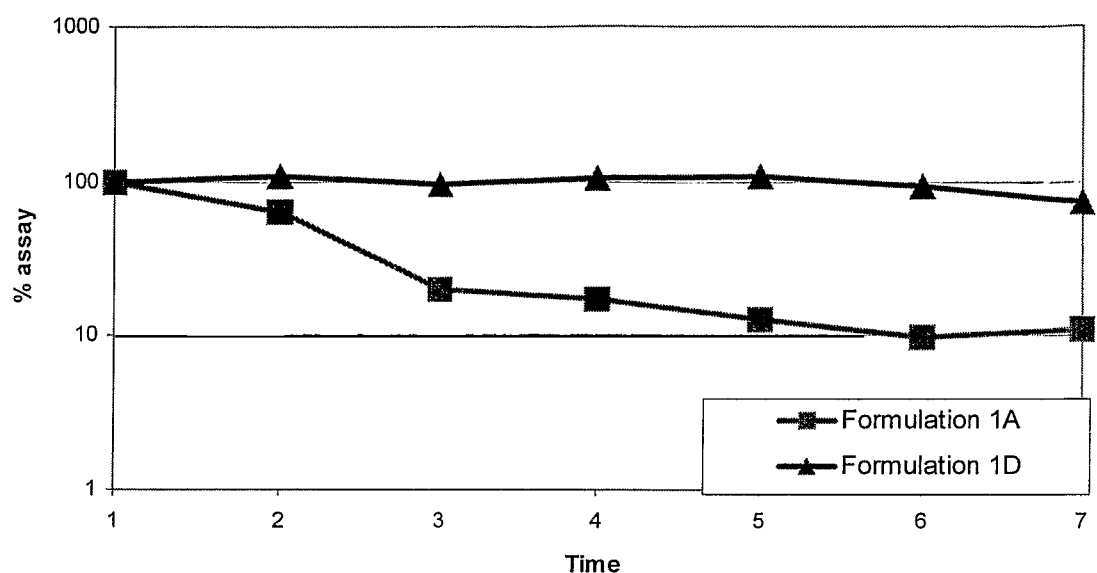

DISPERSIBLE TABLET COMPOSITION

CROSS REFERENCE TO RELATED APPLICATIONS

This application is the U.S. national phase of PCT/IN2006/000291 filed Jul. 24, 2006, which claims the benefit of Indian Patent Application 879/MUM/2005, filed on Jul. 22, 2005, both of which are herein incorporated by reference in their entireties. The PCT application published in English as WO2007/052289 A2.

FIELD OF INVENTION

The present invention relates to a novel dispersible tablet composition of a pharmacologically active ingredient, which rapidly disperses in water to produce a homogeneous dispersion that ensures uniformity of dose and desired therapeutic outcome.

The present invention particularly relates to the selective use of excipients that reduce the sedimentation rate of the pharmacologically active ingredients without compromising the dispersibility of the composition.

BACKGROUND OF INVENTION

Pharmaceutical suspensions are uniform dispersions of solid drug particles in a vehicle in which the drug has minimum solubility. These are usually formulated to improve chemical stability of drug, mask the unpleasant taste and in instances where a liquid dosage form is preferred (easier to swallow, flexibility of administration in a range of doses) over a solid dosage form. Suspension as a dosage form however is associated with issues such as microbial growth, sedimentation and non-uniformity of dose, high cost of manufacturing, difficult to carry etc. For administration of suspensions to children a special oral syringe or dossator needs to be provided which requires care during administration such as proper measurement of the dose, cleaning of the syringe after use, etc. Therefore an alternative dosage form is desired.

Solid oral dosage forms are most convenient from patient as well as from manufacturing chemist's perspective. They ensure uniformity of dosage, are more robust, have less microbiological issues compared to liquid dosage forms. However immediate release tablets cannot act as a substitute for suspension. Thus, there is a need for a formulation, which overcomes the problems associated with the swallowing of solid dosage forms and act as a viable substitute for suspensions. One such dosage form is dispersible tablet. Dispersible tablets as defined in Ph. Eur. are uncoated or film coated tablets intended to be dispersed in water before administration giving a homogeneous dispersion. Typically a dispersible tablet is dispersed in about 5-15 ml of water and the resulting dispersion is administered to the patient. Dispersible tablets are required to disintegrate within 3 minutes in water at 15-25° C. Also the dispersion produced from a dispersible tablet should pass through a sieve screen with a nominal mesh aperture of 710 microns. The dosage form provides advantages of both tablets and liquid formulations. These are convenient to carry, easy to manufacture and more stable.

U.S. Pat. No. 5,256,699 describes a dispersible solid drug formulation of finely divided diclofenac free acid along with a disintegrant and diluent. Dispersible tablets of macrolide antibiotics are described in US patent application 20020061333. U.S. Pat. No. 5,698,226 describes a dispersible tablet of acyclovir or lamotrigine comprising a dispersing agent such as smectite. A dispersible tablet formulation of lamotrigine without use of swellable clay is claimed in PCT application WO 05051350. A roller compression process for production of dispersible tablets of beta lactam antibiotics is discussed in PCT application WO 05115347 whereas direct compression process is elaborated in EP 1086689.

All above-mentioned patents describe dispersible tablets made using varied compositions and processes. However one common limitation of these formulations is settling of the insoluble solids at the bottom or sides of container of the prepared dispersion, which may lead to a loss of part of the drug during administration, resulting in suboptimal dosing.

Sedimentation of particles in a suspension is governed by several factors: particle size, density of the particles and density and viscosity of the vehicle. The velocity of sedimentation of particles in a suspension can be determined by using Stoke's equation:

$$v=[2r^2(D-d)g]/9\eta$$

Where:
v=velocity of sedimentation
r=radius of the particle
g=acceleration of gravity
D=density of the particle
d=density of the vehicle
$\eta$=viscosity of the vehicle According to the Stoke's equation, the velocity of sedimentation of particles in a suspension can be reduced by increasing the viscosity of the vehicle.

PCT application WO0145671 discloses an oral suspension formulation of oxcarbazepine, which attains a viscosity of 5-52 mPas upon shaking. The formulation, however being a suspension, has all the above mentioned limitations. Moreover due to instability of oxcarbazepine, special precautions are required at the manufacturing stage which include purging with nitrogen, inert atmosphere etc. These steps not only complicate the process but also make it time-consuming and expensive.

U.S. Pat. No. 4,886,669 discloses composition of one or more pharmacologically pharmacologically active ingredients in the form of water-dispersible tablet comprising of active ingredient in the form of microparticles. The formulation also contains at least one disintegrant and a swellable material, which generates high viscosity when it comes in contact with water. The microparticles are coated and have a specific size range. Microparticles are prepared for controlled release or taste masking purposes. A special process is employed for manufacturing of the microparticles that is tedious, complicated, and time consuming. To ensure reduced sedimentation, use of high concentrations of polymers is necessary. This may affect the dispersibility. Moreover increase in viscosity alone cannot be regarded as a parameter for dosage form uniformity as there still remains a possibility of sedimentation of high density microparticles. Therefore, the important parameter for uniformity of dosage is the sedimentation rate.

None of the prior art addresses the issue of sedimentation of the active ingredient after formation of a suspension from the dispersible tablet, leading to non-uniformity of dosage. The present inventors have developed a composition of a pharmacologically active ingredient in the form of a dispersible tablet, which, when dispersed in water, gives a homogeneous dispersion with a low sedimentation rate. It is known in the prior art that increasing the viscosity of the vehicle decreases the sedimentation rate. It is also known in the art that use of high viscosity excipients tend to retard the disintegration time of a tablet. It was surprisingly found that selective use excipients in the present invention reduces the sedimentation rate of solids in the dispersion without altering the dispersibility of the composition and ensures uniformity of the dose and thus improves patient compliance.

OBJECT OF INVENTION

It is an object of the present invention to provide a composition of a pharmacologically active ingredient in the form of a dispersible tablet.

It is a further object of the present invention to provide a dispersible tablet composition of a pharmacologically active ingredient, which rapidly disintegrate in water.

It is another object of the present invention to provide a composition of a pharmacologically active ingredient which, when dispersed in water gives a homogeneous dispersion with a low rate of sedimentation.

Yet another object of the present invention is to provide a composition of a pharmacologically active ingredient, which, after dispersion on contact with aqueous medium, shows an increase in the viscosity of the dispersion and reduces sedimentation of the active ingredients thereby ensuring uniformity of dose.

SUMMARY OF INVENTION

According to a preferred aspect of the present invention, there is provided a water-dispersible tablet comprising,
  a pharmacologically active ingredient and
  at least one excipient, which reduces the sedimentation rate of pharmacologically active ingredient According to another aspect of the present invention there is provided a process for the preparation of a dispersible tablet of a pharmacologically active ingredient.

BRIEF DESCRIPTION OF FIGURES

FIG. 1: Sedimentation profile of Formulation 1A and 1D
  Key for Time axis: 1=Initial, 2=0 min, 3=3 min, 4=5 min, 5=10 min, 6=15 min, 7=30 min

DETAILED DESCRIPTION

Typically suspensions have problem of settling of insoluble pharmacologically active ingredient resulting in non-uniformity of dosage. This problem has been addressed by addition of flocculating agents, wetting agents, viscolizers etc. However no such attempts of maintaining uniformity of dosage have been made in the case of dispersion formed using dispersible tablets as these agents may adversely affect the dispersibility of the formulation. It was surprisingly found that the dispersible tablet prepared in accordance with present invention not only achieves rapid disintegration and dispersion but also ensures dosage uniformity.

The term homogeneous dispersion as used herein means that the dispersion produced upon contact with water which ensures the uniformity of pharmacologically active ingredient content for a reasonable period of time.

The term sedimentation rate means the rate at which the pharmacologically active ingredients settle from the dispersion.

The sedimentation rate is determined by the following procedure. 20 tablets are dispersed in water in a 100 ml measuring cylinder, and made up to 100 ml volume. From top 10 ml, 1 ml of dispersion is withdrawn over a time period and assayed for the active ingredient. The desired rate of sedimentation is such that at least 50% of the drug remains in the top 10 ml after 5 min. The formulation can be considered more robust if the desired sedimentation rate is achieved with less than 20 tablets.

The composition of the present invention mainly includes,
  a pharmacologically active ingredient and
    at least one excipient, which reduces sedimentation rate of pharmacologically active ingredient.

In general, the dispersible tablet in accordance with the present invention will include an amount of at least one water-insoluble, pharmacologically active agent in a therapeutically effective amount. As used herein, the terms "water-insoluble" and "insoluble" refer to those substances which are insoluble, practically insoluble, or only slightly or sparingly soluble in aqueous media as those terms are described in the United States Pharmacopeias; Remington's Pharmaceutical Sciences, $18^{th}$ edition published by Mack Publishing Company.

The invention is also applicable to water-soluble drugs that are administered as tablets, and produce viscous dispersion in water prior to administration.

Suitable pharmacologically active ingredients for use in this invention include for example pharmaceuticals, minerals, vitamins and other nutraceuticals, oral care agents, flavorants and mixtures thereof.

A non-exhaustive listing of suitable pharmaceutical actives from which the pharmacologically active ingredient may be chosen include anti-cancer agents. antitussives, antihistamines, decongestants, alkaloids, laxatives, vitamins, antacids, anti-cholesterolemics, anti-lipid agents, antiarrhythmics, antipyretics, analgesics, appetite suppressants, expectorants, anti-anxiety agents, anti-ulcer agents, anti-inflammatory substances, anti-infectives, stimulants, gastrointestinal agents, sedatives. antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hypoglycemic agents, thyroid and antithyroid preparation, diuretics, antispasmodics, uterine relaxants, mineral and nutritional additives, antiobesity drugs, anabolic drugs erythropoietic drugs, antiasthmatics, cough suppressants, mucolytics, anti-uricemic drugs, anti-viral drugs and mixtures thereof.

The pharmacologically active ingredient is selected from calcium carbonate, magnesium hydroxide, magnesium oxide, magnesium carbonate, aluminum hydroxide, sodium bicarbonate, dihydroxyaluminum sodium carbonate, bisacodyl, cascara sagrada, phenolphthalein, famotidine, omeprazole, lansoprazole; sucralfate, misoprostol; prucalopride, clarithromycin, amoxicillin, tetracycline, metronidazole; diphenoxylate, loperamide; glycopyrrolate, ondansetron, ibuprofen, naproxen, ketoprofen. indomethacin, diclofenac, sulindac, tolmetin, mefenamic acid, diflunisal, piroxicam, meloxicam, pseudoephedrine, phenylpropanolamine, chlorpheniramine, dextromethorphan, diphenhydramine, astemizole, terfenadine, fexofenadine, loratadine, desloratadine, cetirizine, carbamazepine, oxcarbazepine, phenyloin, phensuximide, perphenazine, erythromycin, acyclovir, azithromycin, doxycycline, acetaminophen, atovaquone, tamsulosin, oxytetracycline, paroxetine, pentoxifylline, prednisolone, rofecoxib, sulfamethoxazole, sulfisoxazole, tacrolimus, chlorothiazide, chlorpheniramine, ciprofloxacin, clavulanate, fluconazole, griseofulvin, nevirapine, ziprasidone, ceclor, cefdinir, cefpodoxime proxetil, cefprozil, cefibuten, colistin sulfate, megestrol acetate, mesalamine, trovafloxacin mesylate, verapamil hydrochloride, mycophenolate mofetil and pharmaceutically acceptable salts, esters, isomers; and mixtures thereof.

The preferred pharmacologically active ingredients of the present invention are oxcarbazepine, acyclovir, azithromycin, cetirizine, and clarithromycin. Most preferred pharmacologically active ingredient among these is oxcarbazepine which is a poorly soluble drug.

Suitable oral care agents include breath fresheners, tooth whiteners, antimicrobial agents, tooth mineralizers, tooth decay inhibitors, topical anesthetics mucoprotectants. and the like.

Suitable flavorants include menthol, peppermint, mint flavors, fruit flavors. chocolate, vanilla, bubblegum flavors, coffee flavors, liqueur flavors and combinations and the like.

The pharmacologically active ingredient or ingredients are present in a therapeutically effective amount, which is an amount that produces the desired therapeutic response upon oral administration and can be readily determined by one skilled in the art. In determining such amounts, the particular pharmacologically active ingredient being administered, the bioavailability characteristics of the pharmacologically active ingredient, the dose regime, the age and weight of the patient, and other factors must be considered, as known in the art.

The pharmaceutically active ingredient may be any pharmaceutical in the form of its neutral or salt form including prodrugs and metabolites of the drugs, molecular, acid-base and ion-exchange complexes and may be in the form of particle, powder, crystal, granule or microcapsules or mixtures.

The pharmaceutical unit may include along with the pharmaceutically active ingredient other functional components presented for the purpose of modifying the physical, chemical or taste properties of the pharmaceutical. For example the pharmaceutical may be in the form of ion-exchange or cyclodextrin complexes or the pharmaceutical may be included as a mixture or dispersion with various additives such as waxes, lipids, dissolution inhibitors, taste-masking or -suppressing agents, carriers or excipients, and fillers In certain embodiments of the present invention, one or a combination of more than one pharmacologically active ingredients can also be employed.

Other important components of the instant invention are the excipients that reduce the sedimentation rate of the active ingredient. Such excipients may include polymers, waxes, wetting agents or others that interact ionically with the active ingredient.

The preferred excipients for reducing sedimentation rate are hydrophilic polymers. They increase the viscosity of the medium and maintain the wetted particles of the active substance(s) in homogeneous suspension, leading to reduction in their sedimentation rate. These polymers may be used alone or in combination.

Examples of polymers which can be used include but are not limited to: polyalkylene oxides such as polyethylene oxide; cellulose ethers such as hydroxypropylcellulose, hydroxypropyl methyl cellulose, hydroxyethyl cellulose, sodium carboxy methylcellulose, calcium carboxymethyl cellulose, methyl cellulose, ethyl cellulose, microcrystalline cellulose; gums such as gum arabic alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, karaya, whelan; polyols such as propylene glycol, dipropylene glycol, polypropylene glycol, polyethylene glycol (PEG), sorbitol and glycerol; starch and starch-based polymers such as pregelatinized starch, acrylic acid and methacrylic acid polymers, and esters thereof, maleic anhydride polymers; polymaleic acid; poly(acrylamides); poly(olefinic alcohol)s; poly(N-vinyl lactams); polyoxyethylated saccharides; polyoxazolines; polyvinylamines; polyvinylacetates; polyimines; povidone vinylpyrrolidone/vinyl acetate copolymer and polyvinyl acetate, mixture of polyvinyl acetate and polyvinylpyrrolidone, chitin, cyclodextrin, gelatin, chitosan, and combinations thereof.

The preferred hydrophilic polymers are polyethylene oxide, hydroxypropyl cellulose, hydroxypropyl methylcellulose, hydroxyethyl cellulose, sodium carboxy methylcellulose, microcrystalline cellulose, guar gum, xanthan gum, alginates and combinations thereof.

The weight percent of the hydrophilic polymer in the dosage form is about 2 to 75 weight percent, preferably about 10 to 70 weight percent, and most preferably about 5 to 50 weight percent.

The present invention may also include a wetting agent which acts to reduce the surface tension between the aqueous media and the insoluble active, thereby facilitating the active's maintenance in the aqueous media. The wetting agent may be chosen from the broad classes of surfactants, including nonionic, cationic, anionic, and zwitterionic surfactants known in the art. These can include, for example, sorbitan fatty acid esters, polyoxyethylene sorbitan fatty acid esters (Tween®), polyoxyethylene fatty acid esters, polyoxyethylene-polyoxypropylene copolymers and block copolymers.

Disintegrants are particularly important excipients of the present invention as they ensure the rapid dispersibility of the formulation. A careful selection of type and concentration of both hydrophilic polymer and disintegrant ensures rapid disintegration of the tablet with reduced sedimentation rate. The disintegrating agent can be selected from a group including but not limited to the following: starch, sodium starch glycolate, pregelatinised starch, crosslinked polyvinyl pyrrolidone, cross linked calcium or sodium carboxy methyl cellulose, low-substituted hydroxypropyl cellulose microcrystalline cellulose, ion exchange resin, cross-linked polyacrylic acid, alginates, colloidal magnesium-aluminum silicate, calcium silicate and the like. The most preferred being cross linked polyvinyl pyrollidone and calcium silicate. The disintegrant may be present in an amount ranging from about 0.25% to about 50%, more preferably about 0.5 to about 30.0% and most preferably about 1-20% by weight based on the total weight of the composition.

The composition of the invention also typically includes other pharmaceutically acceptable excipients, usually incorporated to ease the manufacturing process as well as to improve the performance of the dosage form. Common excipients include diluents, lubricants, granulating aids, colorants, flavorants, surfactants, pH adjusters, anti-adherents and glidants etc. Such excipients may routinely be incorporated in the dosage forms of this invention.

The present invention may additionally include one or more fillers or excipients in an amount within the range of from about 0 to about 90% by weight and preferably from about 1 to about 80% by weight such as lactose, sugar, corn starch, modified corn starch, mannitol, sorbitol, inorganic salts such as calcium carbonate and/or cellulose derivatives such as wood cellulose and microcrystalline cellulose.

For active ingredients prone to degradation, one or more stabilizers may also be included in the formulation. Stabilizers may include anti-oxidants, pH modulators etc. As used herein, "antioxidant" refers to a substance known to inhibit oxidation. Among preferred antioxidants suitable for use in accordance with the present invention include tocopherol, tocopherol acetate, tocopherol acid succinate, β-carotene, propyl gallate, butylated hydroxytoluene (BHT), butylated hydroxyanisole (BHA), vitamin E, ascorbic acid, sodium ascorbate, calcium ascorbate. ascorbic palmitate, 2,4,5-trihydroxybutyrophenone, 4-hydroxymethyl-2,6-di-tert-butylphenol, erythorbic acid, gum guaiac, thiodipropionic acid, dilauryl thiodipropionate, tert-butylhydroquinone and the like, including pharmaceutically acceptable salts and esters of these compounds. pH modifiers or buffers may also be used to maintain the pH of the final composition within a certain desired range.

As the composition is in the form of a tablet, it may include one or more tableting lubricants in an amount within the range of from about 0.2 to about 8% and preferably from about 0.5 to about 2% by weight of the composition, such as magnesium stearate, stearic acid, palmitic acid, calcium stearate, talc, polyethylene glycol, colloidal silicon dioxide, sodium stearyl fumarate, carnauba wax and the like and mixtures thereof.

For active ingredients having a bitter taste, taste modifying components are employed in an effective amount to produce a consumer acceptable suspension upon disintegration of the dispersible tablet. The amount of taste modifying components required would vary with the amount of pharmaceutical active ingredient used as well as the intensity of the poor taste of the pharmaceutical active ingredient.

Taste modifying compositions in accordance with the invention include but are not limited to sugars, sweet polyhydric alcohols, glycerin, artificial sweetener, flavoring agents and mixtures thereof. Examples of sugars include sucrose, fructose, dextrose, and glucose. Examples of sweet polyhydric alcohols include sorbitol and mannitol. Examples of high intensity sweeteners include aspartame, sucralose, cyclamates, acesulfame potassium, saccharin and mixtures thereof.

Flavorants or flavors may also be used to enhance the organoleptic qualities of the final composition, preferably in synergistic effect with the sweetener(s). Any conventional, approved flavorants may be chosen so long as they do not materially affect the physical or chemical attributes of the active or of the resulting suspension. Both natural and synthetic flavorants are contemplated for use herein. Flavorants can therefore include vanilla, strawberry, cherry, grape, lemon, lime, orange, peppermint, spearmint, cinnamon, and any desired combination thereof. Flavorants will typically be added in amounts of from about 0.005% to about 20%, with about 0.01% to about 5% being especially desirable.

A coloring agent may be selected from any colorant used in pharmaceuticals which is approved and certified by the FDA. It may include Lake of Tartrazine, Lake of Quinoline Yellow, Lake of Sunset Yellow and Lake of Erythrosine, Lack of Carmosine Ponceau. Allura Red, iron oxide red, ion oxide yellow.

The dispersible solid oral dosage forms according to the present invention can be in the form of tablets, capsules, pellets, granules, powders, coated granules, coated pellets etc. The preferred dosage form of the present invention is a tablet. The coated granules or pellets can be filled in capsules or compressed into a tablet.

Tablets in accordance with this invention may be manufactured using conventional tableting techniques like:
1) Direct compression
2) Wet granulation
3) Dry granulation
4) Extrusion/melt granulation The invention is also applicable to orally disintegrating tablets, which disintegrates rapidly in the oral cavity.

While the present invention has been described in terms of its specific embodiments, certain modifications and equivalents will be apparent to those skilled in the art and are intended to be included within the scope of the present invention. The details of the invention, its objects and advantages are explained hereunder in greater detail in relation to non-limiting exemplary illustrations.

EXAMPLES

Example 1

Dispersible Tablets of Oxcarbazepine

| Excipients | A mg/tablet | B mg/tablet | C mg/tablet | D mg/tablet |
|---|---|---|---|---|
| Oxcarbazepine | 300.0 | 300.0 | 300.0 | 300.0 |
| Copovidone (Kollidon VA 64) | 20.0 | 20.0 | 20.0 | 20.0 |
| Microcrystalline cellulose (Avicel PH 102) | 50.0 | 50.0 | 50.0 | 50.0 |
| Sodium starch glycolate (Primojel) | 20.0 | 20.0 | 20.0 | 20.0 |
| Crospovidone (Kollidon CL) | 20.0 | 20.0 | 20.0 | 20.0 |
| Hydroxy propyl methyl cellulose (Methocel K100 LV) | — | 50.0 | — | — |
| Hydroxy ethyl cellulose (Natrosol HHX) | — | — | 50.0 | 150.0 |
| Aerosil 200 | 4.0 | 4.0 | 4.0 | 4.0 |
| Talc | 4.0 | 4.0 | 4.0 | 4.0 |
| Magnesium stearate | 2.0 | 2.0 | 2.0 | 2.0 |
| Total | 420.0 | 470.0 | 470.0 | 520.0 |

Procedure:

Oxcarbazepine, Kollidon VA 64 and Avicel PH 102 were mixed thoroughly and the blend was roll compacted. A fraction of granules between 30 and 40# was collected and mixed with Primojel, Kollidon CL, and the polymer. This mixture was then lubricated using magnesium stearate, Aerosil and talc and compressed into tablets.

| Formulation | Disintegration time |
|---|---|
| A | 12-15 sec |
| B | 90-99 sec |
| C | 15-17 sec |
| D | 120-150 sec |

From above table it is clear that incorporation of polymers does not retard disintegration of tablets as all formulations pass the disintegration test as per Ph. Eur. (4$^{th}$ Edition). The formulations also pass the dispersibility test mentioned in Ph. Eur. (4$^{th}$ Edition).

Example 2

Determination of the Sedimentation Rate

Sedimentation rate of the above formulations was determined as a parameter for uniformity of dose. Five tablets of each of the formulation 1A and 1D were dispersed in 100 ml of water. The 100 ml dispersion was then added in a measuring cylinder and from top 10 ml; 1 ml of dispersion was withdrawn at zero time i.e. immediately after pouring into cylinder and after 3, 5, 10, 15 and 30 min and assayed for oxcarbazepine.

| Time (min) | Assay in Formulation 1A, % label strength | Assay in Formulation 1D, % label strength |
|---|---|---|
| 0 | 63.9 | 109.5 |
| 3 | 20.1 | 95.3 |
| 5 | 17.3 | 104.3 |
| 10 | 12.9 | 107.6 |
| 15 | 9.9 | 92.9 |
| 30 | 10.9 | 74.0 |

It is evident from data above that the formulation without any polymer shows rapid sedimentation of solids (resulting in a concentration in the top 10 ml of less than 25% of nominal within 3 min) whereas in Formulation I D, with 150 mg Natrosol, the drug content stays at more than 90% of the nominal in the top 10 ml for up to 15 min, suggesting minimal sedimentation.

Example 3

Acyclovir Dispersible Tablet

| Excipients | 3A mg/tablet | 3B mg/tablet |
|---|---|---|
| Acyclovir | 200 | 200 |
| Microcrystalline cellulose, USP (Avicel pH 102) | 50 | 50 |
| Sodium starch glycolate, USP (Primojel) | 10 | 10 |
| Povidone, USP (Kollidon K-30) | 10 | 10 |
| Crospovidone, USPNF (Kollidon CL) | 20 | 40 |
| Avicel RC 591 | 60 | — |
| Hypromellose (Methocel E3LV) | — | 20 |
| Sodium Saccharine | 3 | 3 |
| Peppermint flavor | 0.5 | 0.5 |
| Magnesium stearate | 3.5 | 3.5 |
| Total | 357.0 | 337.0 |

Acyclovir, Avicel PH 102, and Primojel were dry mixed and granulated with aqueous solution of Kollidon K30. These granules were dried in tray dryer and blended with Kollidon CL, hydrophilic polymer (Avicel RC 591 or Methocel E3), sodium saccharine, and peppermint flavor. The blend was lubricated using magnesium stearate and compressed into tablets.

In-vitro dissolution rate studies for compositions 3A and 3B were carried out using USP Type II apparatus at 37° C. temperature and 50 rpm. 900 ml of 0.1N HCl was employed as dissolution medium. Both the formulations exhibited more than 85% of the drug release in 15 minutes similar to Zovirax® 200 mg tablets.

Acyclovir dispersible tablet were successfully developed with in vitro release profiles matching with marketed immediate release formulation.

Example 4

Determination of the Sedimentation Rate of Composition 3A and 3B

Ten tablets of each of the formulation 3A and 3B were added to a 100 ml stopper measuring cylinder. Water was added to adjust volume to 100 ml and the cylinder was shaken for about 5 minutes from top 10 ml; 1 ml of dispersion is withdrawn at zero time i.e. immediately after pouring into cylinder and after 5, 10, 15, 30 and 60 min and assayed for acyclovir. At the end of 30 and 60 mins, the measuring cylinder was gently shaken for about 1 min and again 1 ml of dispersion was withdrawn and analyzed.

| Time (min) | Formulation 3A Assay, % label strength | Formulation 3B Assay, % label strength |
|---|---|---|
| 0 | 88.3 | 85.1 |
| 5 | 76.7 | 76.3 |
| 10 | 63.5 | 63.1 |
| 15 | 52.9 | 55.2 |
| 30 | 38.0 | 37.6 |
| 30 (with gentle shaking) | 90.6 | 84.6 |
| 60 | 41.5 | 43.8 |
| 60 (with gentle shaking) | 90.0 | 88.8 |

The acyclovir dispersible tablets exhibited a much reduced sedimentation rate with only 24% of drug settled after 5 minutes. Thus the developed composition ensures uniformity of the drug in the dispersion. Drug assay of 90% after gentle shaking at the end of 30 and 60 min indicate that a flocculated suspension is formed which can be readily redispered. This is particularly of importance in instances where there is a time lag between preparation of dispersion from dispersible tablets and administration to a patient.

Example 5

Clarithromycin Dispersible Tablet

| Excipients | mg/tablet |
|---|---|
| Taste masked clarithromycin complex (equivalent to 125 mg of clarithromycin) | 217.25 |
| Crospovidone, USPNF (Kollidon CL) | 20.00 |
| Microcrystalline cellulose, USP (Avicel PH 102) | 51.92 |
| Hydroxyethyl cellulose, USPNF (Natrosol HHX250) | 70.00 |
| Calcium silicate (Rxcipients FM 1000) | 8.33 |
| Sodium Saccharine | 10.00 |
| Peppermint flavour | 1.00 |
| Orange flavour | 2.00 |
| Magnesium stearate | 2.50 |
| Total | 383.00 |

Taste masked clarithromycin (masked using carbopol and povidone) was dry mixed with Kollidon CL, Avicel PH 102, Natrosol HHX 250, calcium silicate, sodium saccharine and flavours for 10 minutes. The blend was then lubricated with magnesium stearate and compressed into tablets. The disintegration time for these tablets was less than 1 min in a USP disintegration test apparatus.

These dispersible tablets of clarithromycin pass the disintegration and dispersibility tests as per Ph. Eur. (4$^{th}$ Edition).

Example 6

Cetirizine Dispersible Tablet

| Excipients | mg/tablet |
|---|---|
| Cetirizine: ion exchange resin complex | 35.0 |
| Crospovidone, USP NF (Kollidon CL) | 20.0 |
| Microcrystalline cellulose, USP (Avicel pH 102) | 159.0 |
| Carboxymethyl cellulose, USP (Blanose 7 HF) | 20.0 |
| Calcium silicate (Rxcipients FM 1000) | 15.0 |
| Sodium Saccharine | 10.0 |

-continued

| Excipients | mg/tablet |
| --- | --- |
| Peppermint flavour | 1.0 |
| Orange flavour | 2.0 |
| Magnesium stearate | 3.0 |
| Total | 275.0 |

Taste masked cetirizine (ion exchange resin complex) was mixed with Kollidon CL, Avicel pH 102, Blanose 7 HF, calcium silicate, sodium saccharine and flavours. The blend thus obtained was lubricated with magnesium stearate and then compressed into tablets.

Taste masked cetirizine was thus successfully incorporated into a dispersible tablet formulation.

Example 7

Azithromycin Dihydrate Dispersible Tablet

| Excipients | mg/tablet |
| --- | --- |
| Azithromycin dihydrate | 111.70 |
| Crospovidone, USPNF (Kollidon CL) | 18.00 |
| Pregelled starch | 18.00 |
| Microcrystalline cellulose, USP (Avicel PH 102) | 42.00 |
| Croscarmellose sodium, USPNF (Ac-Di-Sol) | 3.55 |
| Sodium Lauryl Sulphate | 0.50 |
| Xanthan Gum | 3.50 |
| Sodium Saccharine | 10.00 |
| Peppermint flavour | 1.00 |
| Orange flavour | 2.00 |
| Magnesium stearate | 2.75 |
| Total | 213.00 |

Azithromycin dihydrate, Kollidon CL, pregelled starch were dry mixed and granulated with water. The granules were dried and mixed with Avicel PH 102, Ac-Di-Sol, sodium lauryl sulphate, xanthan gum, sodium saccharine and flavours. The blend thus obtained was lubricated with magnesium stearate and then compressed into tablets. Incorporation of polymers does not lead to a retardation of disintegration of these tablets pass the disintegration and dispersibility tests as per Ph. Eur. (4$^{th}$ Edition).

The invention claimed is:
1. A dispersible tablet comprising:
   (i) at least one water-insoluble pharmacologically active ingredient;
   (ii) about 5% to about 50% by weight of the composition of hydroxyethyl cellulose to reduces the sedimentation rate of the pharmacologically active ingredient; and
   (iii) about 0.5% to about 20% by weight of the composition of at least one disintegrant;
   wherein the dispersible tablet:
   is capable of disintegrating within 3 minutes in water at 15-25° C.; and
   the dispersible tablet when dispersed in water ensures uniformity of dose.
2. The dispersible tablet of claim 1, further comprising a pharmaceutically acceptable excipient is selected from the group consisting of a filler, a pH modifier, a stabilizer, a taste modifying agent, a flavor, or a colorant.
3. The dispersible tablet composition of 1, wherein the disintegrant is selected from the group consisting of sodium starch glycolate, pregelatinised starch, crosslinked polyvinyl pyrrolidone, cross linked calcium or sodium carboxy methyl cellulose, low-substituted hydroxypropyl cellulose, ion exchange resin, cross-linked polyacrylic acid, alginate, colloidal magnesium-aluminum silicate, or calcium silicate.
4. The dispersible tablet of claim 2, wherein the disintegrant is selected from the group consisting of cross linked polyvinyl pyrrolidone and calcium silicate.
5. A dispersible tablet, comprising:
   (i) oxcarbazepine,
   (ii) about 5 to about 50% by weight hydroxyethyl cellulose, and
   (iii) a combination of cross linked polyvinyl pyrrolidone and calcium silicate;
   wherein the dispersible tablet is:
   capable of disintegrating within 3 minutes in water at 15-25° C.; and
   the dispersible tablet when dispersed in water ensures uniformity of dose.
6. The dispersible tablet of claim 1, wherein said pharmacologically active ingredient is selected from class of anti-cancer agents, antitussives, antihistamines, decongestants, alkaloids, mineral supplements, laxatives, vitamins, antacids, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and antithyroid preparation, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs, anti-viral drugs and mixtures thereof.
7. The dispersible tablet of claim 1, wherein said pharmacologically active ingredient is selected from calcium carbonate, magnesium hydroxide, magnesium oxide, magnesium carbonate, aluminum hydroxide, sodium bicarbonate, dihydroxyaluminum sodium carbonate, bisacodyl, cascara sagrada, phenolphthalein, famotidine, omeprazole, lansoprazole; sucralfate, misoprostol; prucalopride, clarithromycin, amoxicillin, tetracycline, metronidazole; diphenoxylate, loperamide; glycopyrrolate, ondansetron, ibuprofen, naproxen, ketoprofen, indomethacin, diclofenac, sulindac, tolmetin, mefenamic acid, diflunisal, piroxicam, meloxicam, pseudoephedrine, phenylpropanolamine, chlorpheniramine, dextromethorphan, diphenhydramine, astemizole, terfenadine, fexofenadine, loratadine, desloratadine, cetirizine, carbamazepine, oxcarbazepine, phenytoin, phensuximide, perphenazine, erythromycin, acyclovir, azithromycin, doxycycline, acetaminophen, atovaquone, tamsulosin, oxytetracycline, paroxetine, pentoxifylline, prednisolone, rofecoxib, sulfamethoxazole, sulfisoxazole, tacrolimus, chlorothiazide, chlorpheniramine, ciprofloxacin, clavulanate, fluconazole, griseofulvin, nevirapine, ziprasidone, cefaclor, cefdinir, cefpodoxime proxetil, cefprozil, ceftibuten, colistin sulfate, megestrol acetate, mesalamine, trovafloxacin mesylate, verapamil hydrochloride, mycophenolate mofetil and pharmaceutically acceptable salts, esters, isomers, and mixtures thereof.

8. The dispersible tablet of claim 1, wherein said pharmacologically active ingredient is selected from the group consisting of oxcarbazepine, acyclovir, azithromycin, cetirizine, or clarithromycin.

* * * * *